(12) United States Patent
Koehler

(10) Patent No.: US 8,306,183 B2
(45) Date of Patent: Nov. 6, 2012

(54) DETECTION SETUP FOR X-RAY PHASE CONTRAST IMAGING

(75) Inventor: Thomas Koehler, Norderstedt (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 199 days.

(21) Appl. No.: 12/744,070

(22) PCT Filed: Nov. 19, 2008

(86) PCT No.: PCT/IB2008/054852
§ 371 (c)(1),
(2), (4) Date: Jul. 13, 2010

(87) PCT Pub. No.: WO2009/069040
PCT Pub. Date: Jun. 4, 2009

(65) Prior Publication Data
US 2010/0272230 A1   Oct. 28, 2010

(30) Foreign Application Priority Data
Nov. 26, 2007   (EP) ..................................... 07121478

(51) Int. Cl.
*G01N 23/02* (2006.01)
(52) U.S. Cl. .......................................................... 378/36
(58) Field of Classification Search ................ 378/5, 62, 378/87, 9, 63, 70
See application file for complete search history.

(56) References Cited

U.S. PATENT DOCUMENTS

| | | | |
|---|---|---|---|
| 5,173,928 A | 12/1992 | Momose et al. | |
| 7,522,698 B2 * | 4/2009 | Popescu et al. | 378/19 |
| 2001/0038680 A1 * | 11/2001 | Davidson | 378/43 |
| 2002/0150204 A1 * | 10/2002 | Martynov et al. | 378/36 |
| 2005/0226376 A1 | 10/2005 | Yun et al. | |
| 2007/0183560 A1 | 8/2007 | Popescu et al. | |
| 2007/0183580 A1 | 8/2007 | Popescu et al. | |

FOREIGN PATENT DOCUMENTS

| | | |
|---|---|---|
| DE | 102006037257 A1 | 8/2007 |
| EP | 0784202 B1 | 9/2005 |
| EP | 1731099 A1 | 12/2006 |

OTHER PUBLICATIONS

Momose, A.: "Phase-Sensitive Imaging and Phase Tomography Using X-Ray Interferometers"; Optics Express, vol. 11, No. 19, Sep. 2003, pp. 2303-2314.
Weitkamp et al: "X-Ray Phase Imaging With a Grating Interferometer"; Optics Express, vol. 13, No. 16, Aug. 2005, pp. 6293-6304.
Pfeiffer et al: "X-Ray Phase Contrast Imaging Using a Grating Interferometer"; Europhysics News, vol. 37, No. 5, pp. 13-15.
Pfeiffer et al: "Phase Retrieval and Differential Phase-Contrast Imaging With Low-Brilliance X-Ray Sources"; Nature Physics, vol. 2, April 2006, pp. 258-261.

* cited by examiner

*Primary Examiner* — Irakli Kiknadze

(57) ABSTRACT

The invention relates to a method and a device for generating phase contrast X-ray images of an object (1). The device comprises an X-ray source (10) that may for example be realized by a spatially extended emitter (11) behind a grating ($G_0$). A diffractive optical element (DOE), for example a phase grating ($G_1$), generates an interference pattern (I) from the X-radiation that has passed the object (1), and a spectrally resolving X-ray detector (30) is used to measure this interference pattern behind the DOE. Using the information obtained for different wavelengths/energies of X-radiation, the phase shift induced by the object can be reconstructed.

17 Claims, 1 Drawing Sheet

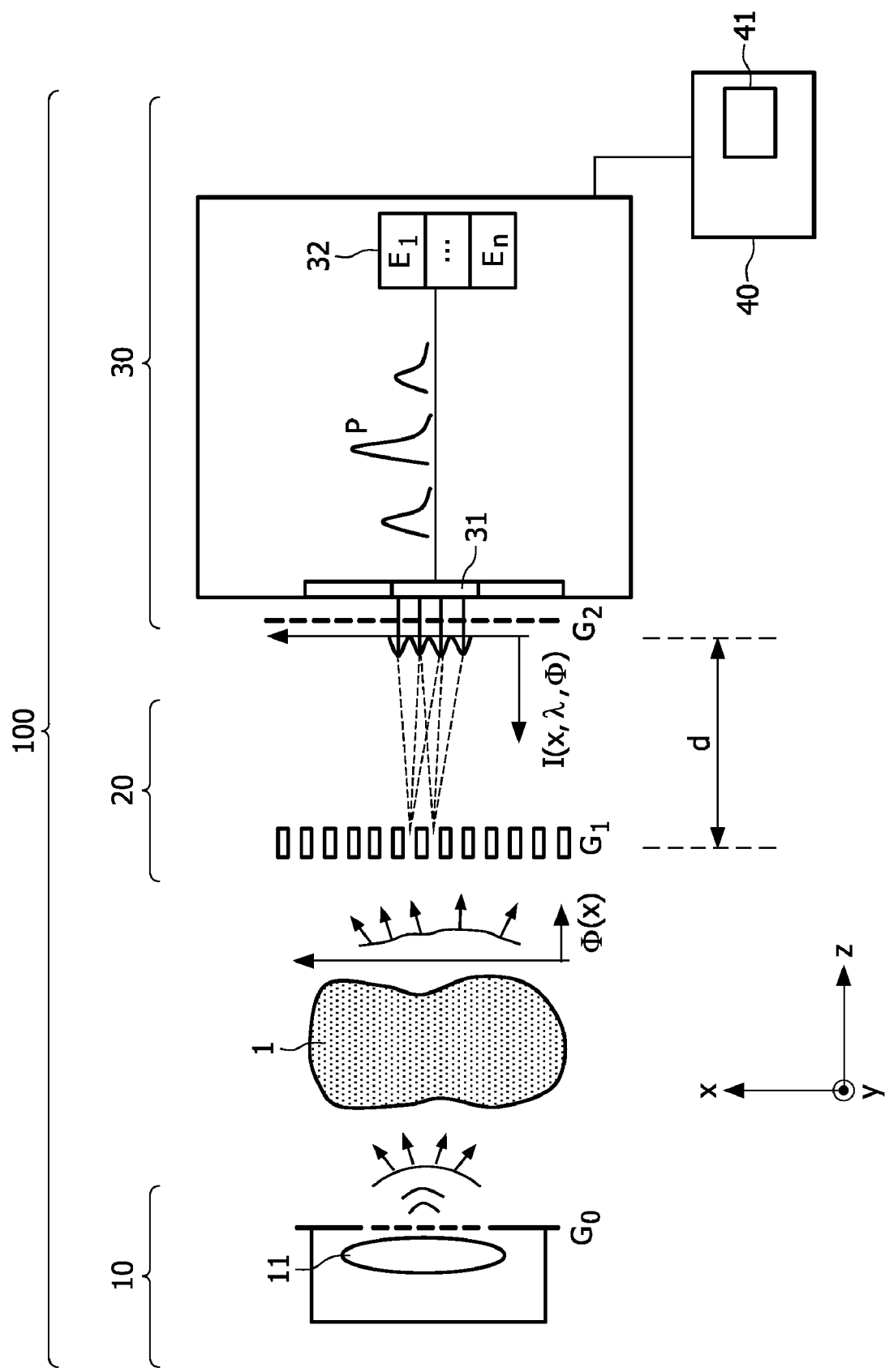

DETECTION SETUP FOR X-RAY PHASE CONTRAST IMAGING

FIELD OF THE INVENTION

The invention relates to an X-ray device and a method for generating phase contrast X-ray images of an object.

BACKGROUND OF THE INVENTION

While classical X-ray imaging measures the absorption of X-rays caused by an object, phase contrast imaging aims at the detection of the phase shift X-rays experience as they pass through an object. According to a design that has been described in literature (T. Weitkamp et al., "X-ray phase imaging with a grating interferometer", Optics Express 13(16), 2005), a phase grating is placed behind an object to generate an interference pattern of intensity maxima and minima when the object is irradiated with (coherent) X-rays. Any phase shift in the X-ray waves that is introduced by the object causes some characteristic displacement in the interference pattern. Measuring these displacements therefore allows to reconstruct the phase shift of the object one is interested in.

A problem of the described approach is that the feasible pixel size of existing X-ray detectors is (much) larger than the distance between the maxima and minima of the interference pattern. These patterns can therefore not directly be spatially resolved. To deal with this issue, it has been proposed to use an absorption grating immediately in front of the detector pixels, thus looking only at small sub-sections of the interference pattern with the pixels of the detector. Shifting the absorption grating with respect to the pixels allows to recover the structure (i.e. the deviation from the default pattern without an object) of the interference pattern. The necessary movement of optical elements is however a nontrivial mechanical task, particularly if it has to be done fast and with high accuracy, as would be required if phase contrast imaging shall be applied in a medical environment.

Based on this background it was an object of the present invention to provide means for generating X-ray phase contrast images of an object that are particularly suited for an application in medical imaging, for example in computed tomography (CT).

SUMMARY OF THE INVENTION

This object is achieved by an X-ray device according to claim 1, a method according to claim 9, a computer program product according to claim 10, a record carrier according to claim 11, and a transmission procedure according to claim 12. Preferred embodiments are disclosed in the dependent claims.

The X-ray device according to the present invention serves for the generation of phase contrast images of an object, i.e. images in which the value of image points is related to the phase shift that is induced in transmitted X-rays by the object, while the position of image points is spatially related to the object (e.g. via a projection or section mapping). The X-ray device comprises the following components:

An X-ray source for generating X-rays. To allow for the generation of interference patterns, the generated X-rays should have a sufficiently large spatial and temporal coherence.

A diffractive optical element, which will be abbreviated "DOE" in the following. The DOE is exposed to the X-ray source, i.e. it is disposed such that it is hit by the emission of the X-ray source if the latter is active.

A spectrally resolving X-ray detector for detecting an interference pattern generated by the DOE.

The described X-ray device has the advantage to extract a maximal amount of information from the interference pattern that is generated by the DOE as this pattern is examined in a spectrally resolved way. This makes it possible to obtain phase contrast images in a fast way, which is particularly advantageous in medical imaging in which the time available for taking an exposure is limited due to various reasons.

Moreover, the described X-ray device allows (or even requires) the application of polychromatic X-ray sources which are the standard sources in medical imaging. In particular, an X-ray source may be used that has an emission bandwidth of more than 10%, preferably about 20-40% with respect to photon energy (meaning that the full width of half maximum of the energy distribution of the X-ray photons is about 20-40% of the energy at the maximum).

The diffractive optical element DOE may be any device that is able to generate the desired interference pattern when irradiated with X-rays. Preferably, the DOE comprises a phase grating, i.e. a grating the lines of which have negligible absorption but substantial phase shift, thus minimizing the loss of X-ray photons.

In principle, the X-ray detector may have one single sensitive element allowing to make a measurement in a corresponding sensitive area. Preferably the detector comprises however an array with a plurality of X-ray sensitive elements (pixels), particularly a one- or two-dimensional array. Measurements can then be made simultaneously at a plurality of positions, allowing for example to sample a spatially resolved two-dimensional projection image in one step.

In another embodiment of the invention, the X-ray detector comprises a modulator for modulating its spatial sensitivity with a periodicity having a fixed relationship to a periodicity of the DOE (e.g. having substantially twice the periodicity of the latter). The application of such a modulator is particularly useful in combination with usual X-ray sensitive elements (e.g. pixels comprising a scintillator with an associated photodetector or pixels comprising a directly converting material) because the latter have a size which is typically much larger than the pitch of an interference pattern. In this case, the modulator can be used to increase the spatial resolution of the X-ray detector to the limit given by the periodicity of the interference pattern. The modulator may for example be realized by an absorption grating or by a scintillation structure as described in US 2007/0183580 A1.

The X-ray device preferably further comprises an evaluation unit for determining the phase shift caused by an object that is disposed in the path of the X-rays between the X-ray source and the DOE. The evaluation unit may optionally be realized by dedicated electronic hardware, digital data processing hardware with associated software, or a mixture of both. The evaluation unit exploits the fact that there is a well-defined relationship between the phase shift induced by an object and the resulting changes in the interference pattern that can be observed behind the DOE; inverting this relationship allows to calculate the desired phase contrast image of the object.

In a further development of the aforementioned embodiment, the evaluation unit additionally comprises a reconstruction module for reconstructing cross-sectional phase contrast images of an object from phase contrast projections of said object which were taken from different directions. The reconstruction module may apply algorithms of computed tomography (CT) which are well-known for a person skilled in the art of absorption X-ray imaging.

It was already mentioned that the X-ray source should have the temporal and spatial coherence that is necessary for the generation of an interference pattern behind the DOE. The X-ray source may optionally comprise a spatially extended emitter that is disposed behind a grating, wherein the term "behind" refers to the emission direction of the X-ray source (i.e. emitted X-rays pass through the grating). The extended emitter can be a standard anode as it is used in conventional X-ray sources and may by itself be spatially incoherent. With the help of the grating, the emitter is effectively divided in a number of line emitters each of which is spatially coherent (in a direction perpendicular to its length).

The X-ray source may optionally comprise at least one filter, e.g. a filter which suppresses a certain band of the X-ray spectrum emitted by the X-ray source. Parts of the X-ray spectrum that are of no use for the desired phase contrast imaging or that even disturb such an imaging can thus be blended out. This helps to minimize the exposure of the object to X-radiation, which is particularly important in medical applications.

The invention further relates to a method for generating X-ray phase contrast images of an object, said method comprising the following steps:

Irradiating the object with polychromatic X-radiation.

Generating an interference pattern with a diffractive optical element (DOE) disposed behind the object, wherein the term "behind" refers to the propagation direction of the applied X-radiation.

Detecting said interference pattern in a spectrally resolved way, i.e. discriminating the photon energy of the X-rays with respect to at least one threshold (e.g. "lower than 70 keV" or "higher than 70 keV").

Determining the phase shift caused by the object based on the detected interference pattern.

The X-ray device will typically be programmable, e.g. it may include a microprocessor or an FPGA. Accordingly, the present invention further includes a computer program product which provides the functionality of any of the methods according to the present invention when executed on a computing device.

Further, the present invention includes a data carrier, for example a floppy disk, a hard disk, or a compact disc (CD-ROM), which stores the computer product in a machine readable form and which executes at least one of the methods of the invention when the program stored on the data carrier is executed on a computing device.

Nowadays, such software is often offered on the Internet or a company Intranet for download, hence the present invention also includes transmitting the computer product according to the present invention over a local or wide area network. The computing device may include a personal computer or a work station. The computing device may include one of a microprocessor and an FPGA.

The above method, computer program product, data carrier and transmission procedure comprise as an essential component the concept of the X-ray device described above. Reference is therefore made to the above description for more information about the details, advantages and modifications of these elements.

DETAILED DESCRIPTION OF EMBODIMENTS

These and other aspects of the invention will be apparent from and elucidated with reference to the embodiment(s) described hereinafter. These embodiments will be described by way of example with the help of the accompanying single drawing which schematically illustrates an X-ray device according to the present invention for generating phase contrast images of an object.

Phase contrast X-ray imaging aims at the measurement of the phase shift of X-rays as they pass through an object. The benefit of phase sensitive measurements is that the phase contrast is potentially orders of magnitude higher than the absorption contrast (cf. A. Momose, "Phase sensitive imaging and phase tomography using X-ray interferometers", Optics Express 11(19), 2003; T. Weitkamp et al., "X-ray phase imaging with a grating interferometer", Optics Express 13(16), 2005). Initially a major shortcoming of phase sensitive methods was that X-ray sources with a very narrow bandwidth were required. This shortcoming could however be overcome by using standard X-ray tubes with a special filter to achieve a bandwidth of 10%-20% (cf. F. Pfeiffer et al., "Phase retrieval and differential phase contrast imaging with low-brilliance X-ray sources", Nature Physics 2, pp 258-261, 2006).

In order to measure the phase of X-rays with the known setups, at least three independent measurements of each geometrical ray are required, where at least one of several grids has to be displaced perpendicular to the optical axis by fractions of its grid constant. Tomography may be performed in these approaches using a rotating object, where the measurements are taken at a stationary relative position of the measurement setup. However, for a medical tomography system, it is mandatory that the data acquisition is performed using a system that rotates continuously around the object (patient). Furthermore, in a medical tomography system grid movements need to be performed not only precisely, but also rather quickly, which is very hard to perform.

The accompanying FIG. 1 illustrates an X-ray device 100 that addresses the above issues. The X-ray device 100 comprises an X-ray source 10 for generating polychromatic X-radiation. The X-ray source 10 comprises in a casing a spatially extended emitter 11 that can for example be realized by the focus (anode) of a standard "broadband" X-ray source and that typically has an extension of several millimeters perpendicular to the optical axis (z-axis). A grating $G_0$ is disposed in front of the emitter 11 to subdivide the emission in lines each of which is spatially coherent in transverse direction. More details about this approach can be found in literature (e.g. Pfeiffer et al., above).

For purposes of clarity, only one cylindrical wave propagating in z-direction behind one slit of the grating $G_0$ is illustrated in FIG. 1. The cylindrical wave passes through an object 1, for example the body of a patient, that shall be imaged by the device 100. The material of the object 1 induces a phase shift in the X-ray wave, resulting in an altered (disturbed) wave front behind the object 1. For each position x perpendicular to the optical axis, a phase shift $\Phi(x)$ is thus associated to the wave front that is characteristic of the material properties along the corresponding X-ray path. The complete function $\Phi$ is a phase contrast projection image of the object 1 one is interested in.

In order to determine the phase shift function $\Phi$, a diffractive optical element (DOE) is disposed behind the object 1. In the shown example, this DOE is realized by a phase grating $G_1$ extending perpendicular to the optical axis (with its slits parallel to the slits of the source grating $G_0$). The grating $G_1$ generates an interference pattern in transmission geometry, i.e. in the space opposite to the object side. This interference pattern can, at fixed coordinates y and z, be characterized by a function $$I = I(x, \lambda, \Phi(x)),$$

wherein $\lambda$ is the X-ray wavelength at which the spectral intensity I of the interference pattern is observed.

At a given distance d from the DOE grating $G_1$ and for a particular wavelength X, the interference pattern will correspond to a periodic pattern of intensity maxima and minima as schematically illustrated in FIG. 1. Measuring this interference pattern with an X-ray detector 30 will then allow to infer the phase shifts $\Phi(x)$ that were introduced by the object 1.

In practice, the measurement of the interference pattern I at a distance d from the grid $G_1$ is however a nontrivial task as the required spatial resolution, determined by the distance between two adjacent maxima or minima, is much smaller than the size of the sensitive elements or pixels 31 of usual X-ray detectors. To address this problem, it has been proposed in literature to place an absorption grating $G_2$ immediately in front of the detector pixels 31, said grating having essentially the same periodicity as the grid $G_1$ behind the object. The absorption grating $G_2$ has the effect to provide small windows through which the detector "looks" at corresponding subsections of the periodic interference pattern I, for example at small regions around the maxima, thus effectively measuring the intensity in these subsections. By shifting the grating $G_2$ in x-direction, the interference pattern can be sampled at several positions, which allows to reconstruct it completely.

A problem of the described grid-stepping approach is that it requires a complicated and precise mechanics. Moreover, the stepping implies that the measurements are made sequentially at different times, which is disadvantageous if the object moves or if a rotational setup shall be used for computed tomography (CT) reconstructions.

In order to avoid these problems, it is proposed here to measure the interference pattern I $(x, \lambda, \Phi)$ for one position of the grating $G_2$ only but for different energies or wavelengths $\lambda$ simultaneously using an energy-resolving X-ray detector 30. Such energy-resolving detectors are well-know in the art. They may for example apply pulse counting and pulse discrimination, i.e. every X-ray photon absorbed by a pixel 31 is converted into an electrical pulse P, the height of which corresponds to the energy of the photon. The pulses P can readily be counted and classified by a discriminator 32 with respect to a number of different energy levels $E_1, \ldots E_n$.

The measurements of the X-ray detector 30 can be evaluated by an evaluation 40, for example a digital data processing unit (workstation) with appropriate software. This unit may particularly comprise a reconstruction module 41 for executing CT reconstructions from phase contrast projections of the object 1 that were generated from different rotational directions around it.

The described approach has several advantages, for example:
The mechanical modulation of gratings becomes obsolete.
The tube power of the X-ray source 10 is used more efficiently since a broader X-ray spectrum can be used (because the narrow bandwidth in the order of 10% is implemented on the detection side).
The interference pattern for each energy is measured truly in the same geometry.

Finally it is pointed out that in the present application the term "comprising" does not exclude other elements or steps, that "a" or "an" does not exclude a plurality, and that a single processor or other unit may fulfill the functions of several means. The invention resides in each and every novel characteristic feature and each and every combination of characteristic features. Moreover, reference signs in the claims shall not be construed as limiting their scope.

The invention claimed is:

1. An X-ray device for generating phase contrast images of an object, comprising:
    an X-ray source;
    a diffractive optical element (DOE) exposed to the X-ray source; and
    a spectrally resolving X-ray detector for detecting interference patterns generated by the DOE.

2. The X-ray device according to claim 1, wherein the X-ray source has an emission bandwidth of 20-40%.

3. The X ray device according to claim 1, wherein the DOE comprises a phase grating.

4. The X ray device according to claim 1, wherein the X-ray detector comprises an array of X-ray sensitive elements.

5. The X ray device according to claim 1, wherein the X-ray detector comprises a modulator for modulating spatial sensitivity of the detector with a periodicity corresponding to a periodicity of the DOE.

6. The X ray device according to claim 1, wherein the device comprises an evaluation unit for determining the phase shift caused by an object in the path of the X-rays from the X-ray source to the X-ray detector.

7. The X ray device according to claim 6, wherein the evaluation unit comprises a reconstruction module for reconstructing a cross-sectional phase contrast image of an object from phase contrast projections of the object taken from different directions.

8. The X ray device according to claim 1, wherein the X-ray source comprises a spatially extended emitter disposed behind a grating.

9. The system of claim 1, wherein the spectrally resolving X-ray detector detects interference patterns by discriminating a photon energy of the x-rays with respect to at least one threshold.

10. The system of claim 1, wherein the spectrally resolving X-ray detector employs pulse counting and pulse discrimination.

11. The system of claim 1, wherein each photon absorbed by each pixel of the spectrally resolving X-ray detector is converted into an electrical pulse, wherein a height of the electrical pulse corresponds to an energy of the photon.

12. The system of claim 11, further comprising a discriminator that counts each electrical pulse and classifies each electrical pulse according to different energy levels.

13. A method for generating X-ray phase contrast images of an object, comprising the following steps:
    irradiating the object with polychromatic X-radiation;
    generating an interference pattern with a diffractive optical element, called DOE, disposed behind the object;
    detecting the interference pattern in a spectrally resolved way; and
    determining the phase shift caused by the object based on the detected interference pattern.

14. A non-transitory computer program product for enabling carrying out a method according to claim 13.

15. The system of claim 13, wherein the determining in a spectrally resolved way includes converting each absorbed photon into an electrical pulse, wherein a height of the electrical pulse corresponds to an energy of the photon.

16. The method of claim 13, further comprising modulating spatial sensitivity with a periodicity corresponding to a periodicity of the DOE.

17. The method of claim 13, further comprising reconstructing a cross-sectional phase contrast image of an object from phase contrast projections of the object taken from different directions.

* * * * *